United States Patent
Lei et al.

(10) Patent No.: US 7,368,422 B2
(45) Date of Patent: May 6, 2008

(54) SEMI-SYNTHETIC REARRANGED VANCOMYCIN/DESMETHYL-VANCOMYCIN-BASED GLYCOPEPTIDES WITH ANTIBIOTIC ACTIVITY

(75) Inventors: Yaohui Lei, Hebei (CN); Yu Bai, Hebei (CN); Daniel Chu, Santa Clara, CA (US); Zhi-Jie Ni, Fremont, CA (US); John Jian-Xin Wang, Oakland, CA (US)

(73) Assignee: Novartis Vaccines and Diagnostics Inc., Emeryville, CA (US)

( * ) Notice: Subject to any disclaimer, the term of this patent is extended or adjusted under 35 U.S.C. 154(b) by 0 days.

(21) Appl. No.: 11/361,311

(22) Filed: Feb. 24, 2006

(65) Prior Publication Data

US 2007/0021328 A1 Jan. 25, 2007

Related U.S. Application Data

(60) Provisional application No. 60/657,636, filed on Feb. 28, 2005.

(51) Int. Cl.
*A61K 38/02* (2006.01)
*A61K 38/12* (2006.01)
*A61K 31/70* (2006.01)
*C07K 7/64* (2006.01)
*C07K 9/00* (2006.01)
*C07K 5/12* (2006.01)

(52) U.S. Cl. ............... 514/8; 514/9; 514/23; 530/317; 530/322

(58) Field of Classification Search ............. None
See application file for complete search history.

(56) References Cited

U.S. PATENT DOCUMENTS

| 5,488,131 | A | 1/1996 | Myers | |
| 5,840,684 | A | 11/1998 | Cooper et al. | 514/11 |
| 6,841,661 | B2 | 1/2005 | Kim et al. | |
| 2003/0008812 | A1 | 1/2003 | Christensen et al. | |
| 2004/0136947 | A1 | 7/2004 | Zhao et al. | |
| 2004/0259228 | A1 | 12/2004 | Thorson | |
| 2006/0276623 | A1 | 12/2006 | Chu et al. | |

FOREIGN PATENT DOCUMENTS

WO WO 2004/019970 3/2004

OTHER PUBLICATIONS

A. Malabarba et al. Med. Res. Rev. (1997) 17(1), pp. 69-137.*
S.R. Vippagunta, et al. Adv. Drug Delivery Rev. (2001) 48, pp. 3-26.*
J. March Organic Chemistry, 3rd Ed. (1985), pp. 66-70, 82-119 and 1024-1026.*
S. Majumdar and A.K. Mitra. Expert Opin. Drug Delivery (2006) 3(4), p. 511-527.*
Nagarajan et al., "Synthesis and Antibacterial Activity of N-Acyl Vancomycins" *J. Antibiotics* 41(10) :1430-1438, Oct. 1988.
Berge et al., Journal of Pharmaceutical Sciences, vol. 66, No. 1, Jan. 1977, pp. 1-19.
Pavlov et al., "A New Type of Chemical Modification of Glycopeptides Antibiotics: Aminomethylated Derivatives of Eremomycin and Their Antibacterial Activity", The Journal of Antibiotics, vol. 50, No. 6, Jun. 1997, pp. 509-513.
International patent application No. PCT/US06/07021, International Search Report dated Nov. 28, 2006.
International patent application No. PCT/US06/07021, Written Opinion dated Nov. 28, 2006.
Feliu, L. et al., Cyclic Peptides Containing Biaryl and Biaryl Ether Linkages, *International Journal of Peptide Research and Therapeutics*, vol. 11, No. 1, Mar. 2005, pp. 53-97.
Jia, Y. et al. Identification of synthetic compounds active against VRE: the role of the lapidated aminoglucose and the structure of glycopeptide binding pocket, *Bioorganic & Medicinal Chemistry Letters*, 15, (2005) 4594-4599.
U.S. Appl. No. 11/361,852, entitled *Semi-Synthetic Desmethyl-Vancomycin-Based Glycopeptides with Antibiotic Activity*, Chu et al., filed Feb. 24, 2006.

* cited by examiner

*Primary Examiner*—Andrew D. Kosar
(74) *Attorney, Agent, or Firm*—Beyer Weaver LLP

(57) ABSTRACT

Semi-synthetic glycopeptides that have antibacterial activity are based on modifications of a rearranged vancomycin or desmethyl-vancomycin scaffold, in particular, alkylation or acylation of the amino substituent on the amino-substituted sugar moiety on this scaffold with certain acyl groups; and/or conversion of the acid moiety on the macrocyclic ring of this scaffolds to certain substituted amides. Also provided are methods for synthesis of the compounds, pharmaceutical compositions containing the compounds, and methods of use of the compounds for the treatment and/or prophylaxis of diseases, especially bacterial infections.

2 Claims, 3 Drawing Sheets

SEMI-SYNTHETIC REARRANGED VANCOMYCIN/DESMETHYL-VANCOMYCIN-BASED GLYCOPEPTIDES WITH ANTIBIOTIC ACTIVITY

CROSS-REFERENCE TO RELATED APPLICATIONS

This application claims priority to U.S. Provisional Patent Application No. 60/657,636, filed Feb. 28, 2005, titled SEMI-SYNTHETIC REARRANGED VANCOMYCIN/DESMETHYL-VANCOMYCIN-BASED GLYCOPEPTIDES WITH ANTIBIOTIC ACTIVITY, the disclosure of which is incorporated herein by reference in its entirety and for all purposes.

BACKGROUND OF THE INVENTION

1. Field of the Invention

This invention relates to novel semi-synthetic glycopeptides having antibacterial activity, to pharmaceutical compositions comprising these compounds, and to a medical method of treatment.

2. Description of Related Art

The emergence of drug resistant bacterial strains has highlighted the need for synthesizing and identifying antibiotics with improved activity. Naturally occurring glycopeptide antibiotics used to combat bacterial infections include vancomycin and desmethyl-vancomycin compounds having the following structure:

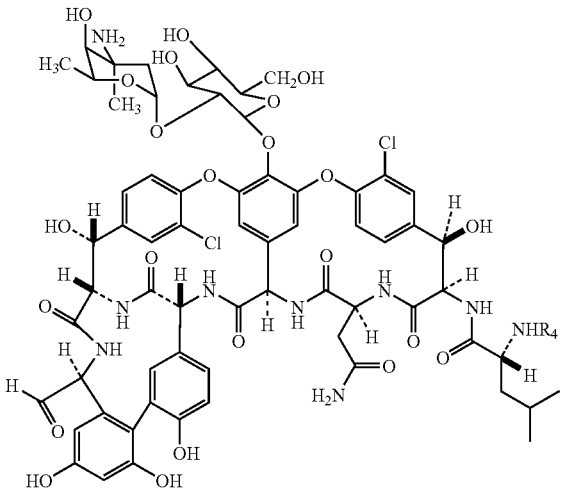

wherein $R_4$ is $CH_3$ for vancomycin, and H for desmethyl-vancomycin.

These compounds are used to treat and prevent bacterial infection, but as with other antibacterial agents, bacterial strains having resistance or insufficient susceptibility to these compounds have been identified, and these compounds have been found to have limited effect against certain bacterial caused by glycopeptide resistant enterococci. Therefore, there is a continuing need to identify new derivative compounds which possess improved antibacterial activity, which have less potential for developing resistance, which possess improved effectiveness against bacterial infections that resist treatment with currently available antibiotics, or which possess unexpected selectivity against target microorganisms.

SUMMARY OF THE INVENTION

To achieve the foregoing, the present invention provides novel semi-synthetic glycopeptides that have antibacterial activity. The semi-synthetic glycopeptides of the invention are based on modifications of a rearranged vancomycin or desmethyl-vancomycin scaffold, in particular, acylation or alkylation of the amino substituent on the amino-substituted sugar moiety on this scaffold with certain acyl or alkyl groups; and/or conversion of the acid moiety on the macrocyclic ring of this scaffolds to certain substituted amides. Also provided are methods for synthesis of the compounds, pharmaceutical compositions containing the compounds, and methods of use of the compounds for the treatment and/or prophylaxis of diseases, especially bacterial infections.

In specific embodiments of the invention, the rearranged vancomycin or desmethyl-vancomycin scaffold is modified to make compounds having the formula:

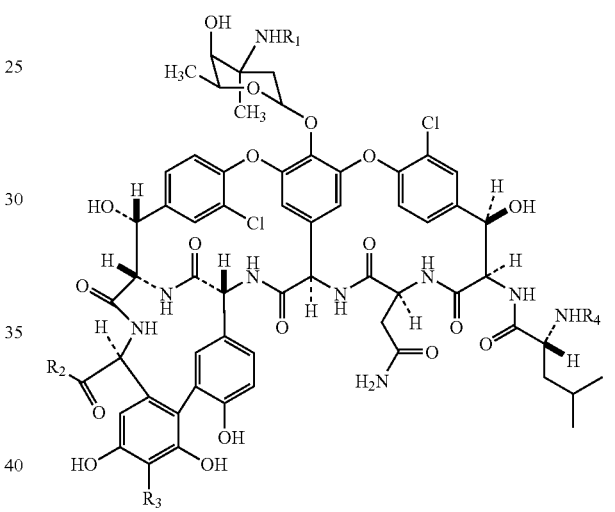

(I)

wherein, $R_1$ is selected from the group consisting of H, $CHR_5R_{5a}$, $C(=O)R_6$ and $C(=O)CR_7R_{7a}NR_8R_{8a}$, wherein, $R_5$ and $R_{5a}$ are independently selected from the group consisting of hydrogen and unsubstituted or substituted alkyl, alkenyl, cycloalkyl, cycloalkenyl, heterocycloalkyl, aryl, arylalkyl, alkylaryl, and heteroaryl, said aryl, alkylaryl, arylalkyl or heteroaryl group optionally containing one or more optionally substituted aryl, heteroaryl, or condensed rings, or $R_5$ and $R_{5a}$ together with the atom to which they are attached form a cycloalkyl ring which optionally contains a heteroatom selected from the group consisting of optionally substituted O, N, and S, $R_6$ is selected from the group consisting of unsubstituted or substituted alkyl, alkenyl, cycloalkyl, cycloalkenyl, heterocycloalkyl, aryl, arylalkyl, alkylaryl, and heteroaryl, said aryl, alkylaryl, arylalkyl or heteroaryl group optionally containing one or more optionally substituted aryl, heteroaryl, or condensed rings, $R_7$ and $R_{7a}$ are independently hydrogen, the side chain of a naturally occurring or non-naturally occurring amino acid, alkyl, or alkyl substituted with one or more substituents selected from the group consisting of halogen, hydroxy, alkoxy, alkoxyalkoxy, carboxyl, carboxyl ester, —C(═O)NR$_8$R$_{8a}$, —NR$_8$R$_{8a}$, aryl, substituted aryl, heteroaryl, substituted heteroaryl, mercapto, or thioalkoxy, or R$_7$ and R$_{7a}$ together with the atom to which they are attached form a cycloalkyl ring which optionally contains a heteroatom selected from the group consisting of optionally substituted O, N, and S, R$_8$ and R$_{8a}$ are independently selected from the group consisting of hydrogen and unsubstituted or substituted alkyl, alkenyl, cycloalkyl, cycloalkenyl, heterocycloalkyl, aryl, arylalkyl, alkylaryl, and heteroaryl, said aryl, alkylaryl, arylalkyl or heteroaryl group optionally containing one or more optionally substituted aryl, heteroaryl, or condensed rings, or R$_8$ and R$_{8a}$ together with the atom to which they are attached form a cycloalkyl ring which optionally contains a heteroatom selected from the group consisting of optionally substituted O, N, and S;

R$_2$ is selected from the group consisting of,
(1) OH,
(2) 1-adamantanamino,
(3) 2-adamantanamino,
(4) 3-amino-1-adamantanamino,
(5) 1-amino-3-adamantanamino,
(6) 3-loweralkylamino-1-adamantanamino,
(7) 1-loweralkylamino-3-adamantanamino,
(8) amino,
(9) NR$_9$R$_{9a}$ wherein R$_9$ and R$_{9a}$ are independently selected from the group consisting of hydrogen, loweralkyl or substituted loweralkyl, or R$_9$ and R$_{9a}$ together with the atom to which they are attached form a 3-10 membered heterocycloalkyl ring, which may optionally be substituted with one or more substituents independently selected from the group consisting of
(a) halogen,
(b) hydroxy,
(c) C$_1$-C$_3$-alkoxy,
(d) C$_1$-C$_3$-alkoxy-C$_1$-C$_3$-alkoxy,
(e) oxo,
(f) C$_1$-C$_3$-alkyl,
(g) halo-C$_1$-C$_3$-alkyl, and
(h) C$_1$-C$_3$-alkoxy-C$_1$-C$_3$-alkyl;

R$_3$ is selected from the group consisting of hydrogen and aminoloweralkyl, wherein the aminoloweralkyl amino group is further substituted with unsubstituted or substituted alkyl, alkenyl, cycloalkyl, cycloalkenyl, aryl, arylalkyl, alkylaryl, alkoxy, aryloxy, substituted alkoxy, and substituted aryloxy; and R$_4$ is selected from the group consisting of hydrogen and methyl;

or a pharmaceutically acceptable salt, ester, solvate, stereoisomer, tautomer or prodrug thereof.

The present invention also provides pharmaceutical compositions which comprise a therapeutically effective amount of a compound as defined above in combination with a pharmaceutically acceptable carrier.

The invention further relates to methods of treating bacterial infections in a host mammal in need of such treatment comprising administering to a mammal in need of such treatment a therapeutically effective amount of a compound of the invention as defined above.

In a further aspect of the present invention are provided processes for the preparation of semi-synthetic glycopeptides of formula (I), above.

BRIEF DESCRIPTION OP THE DRAWINGS

Figure 1:
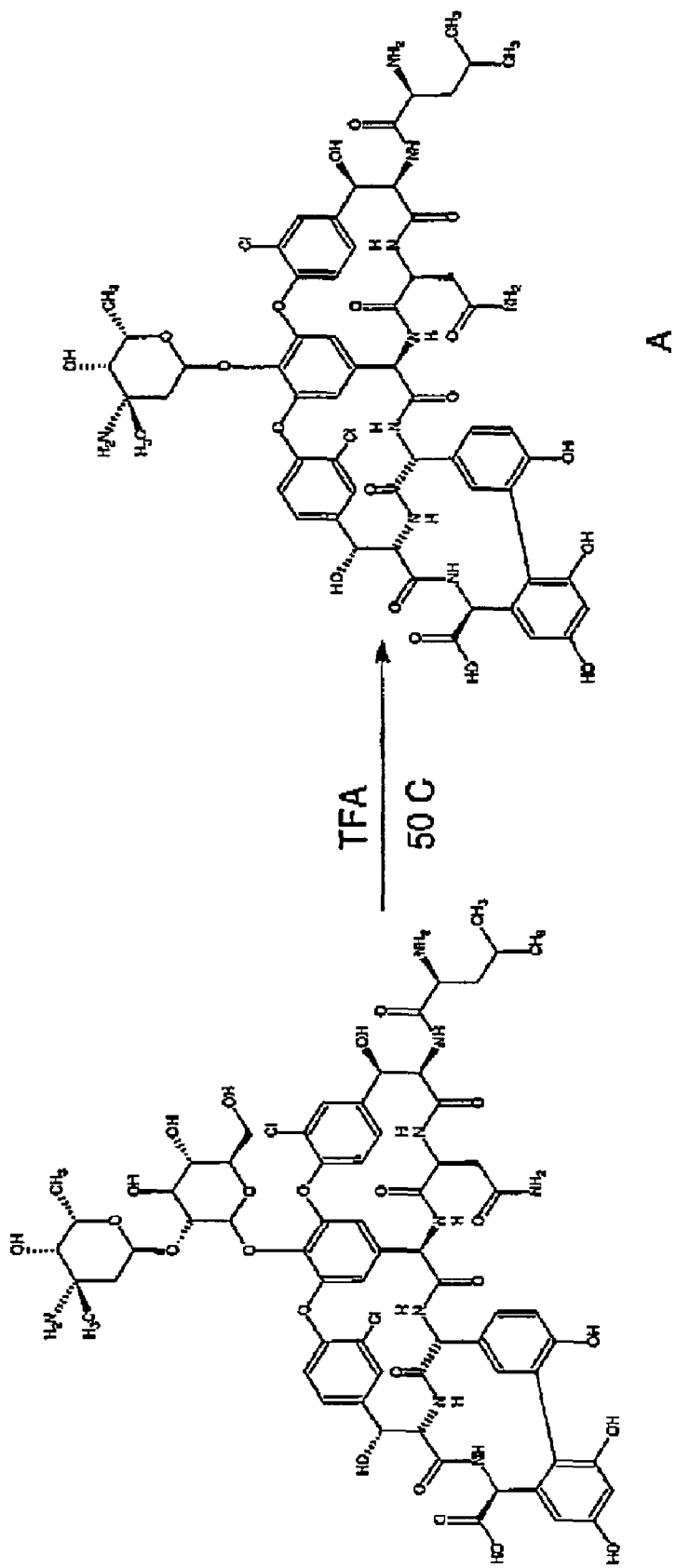
FIG. 1 is an example of a synthetic scheme for obtaining a starting material for preparing a compound in accordance with the present invention.
Figure 2A:
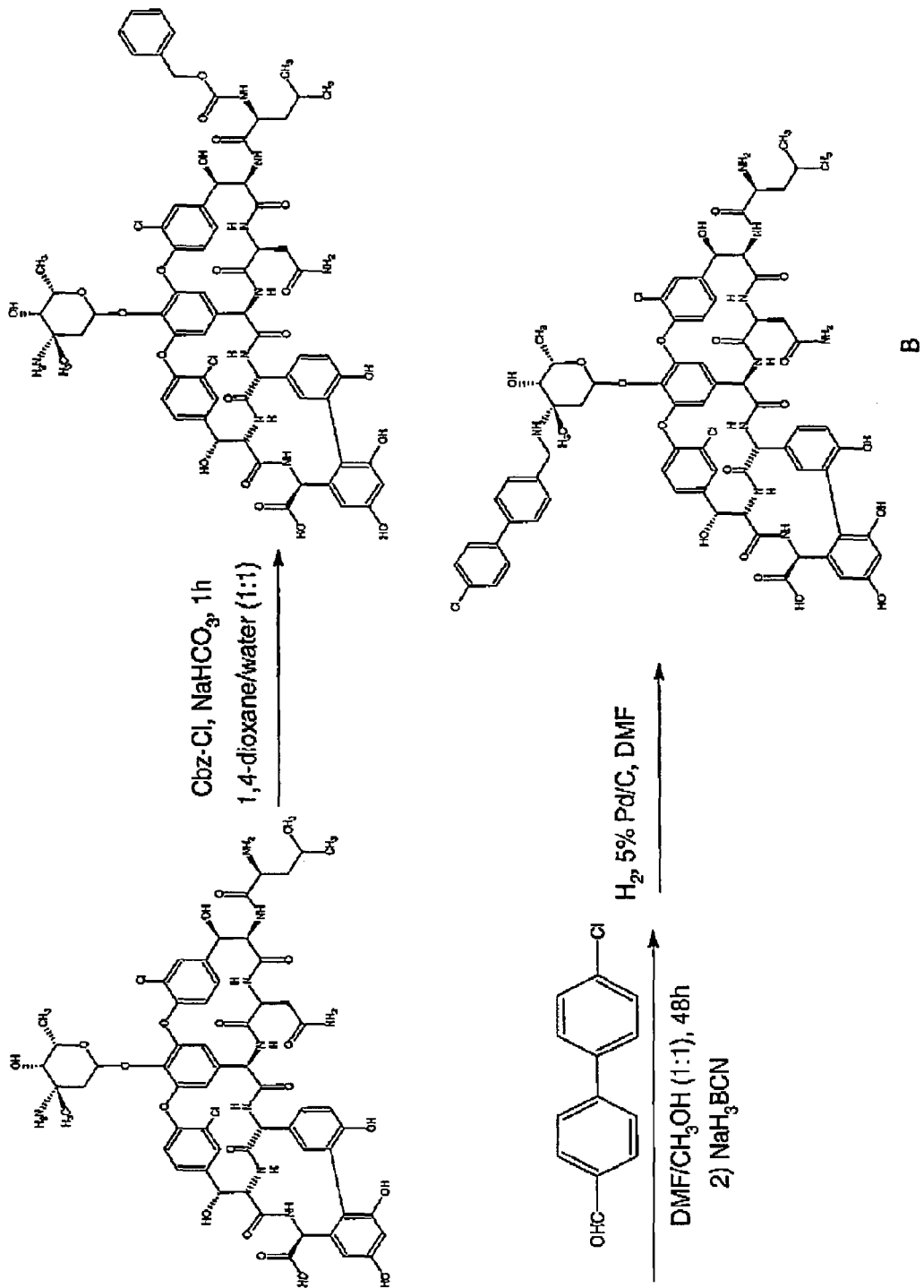
FIG. 2A is an example of a synthetic scheme for preparing a compound in accordance with the present invention.
Figure 2B:
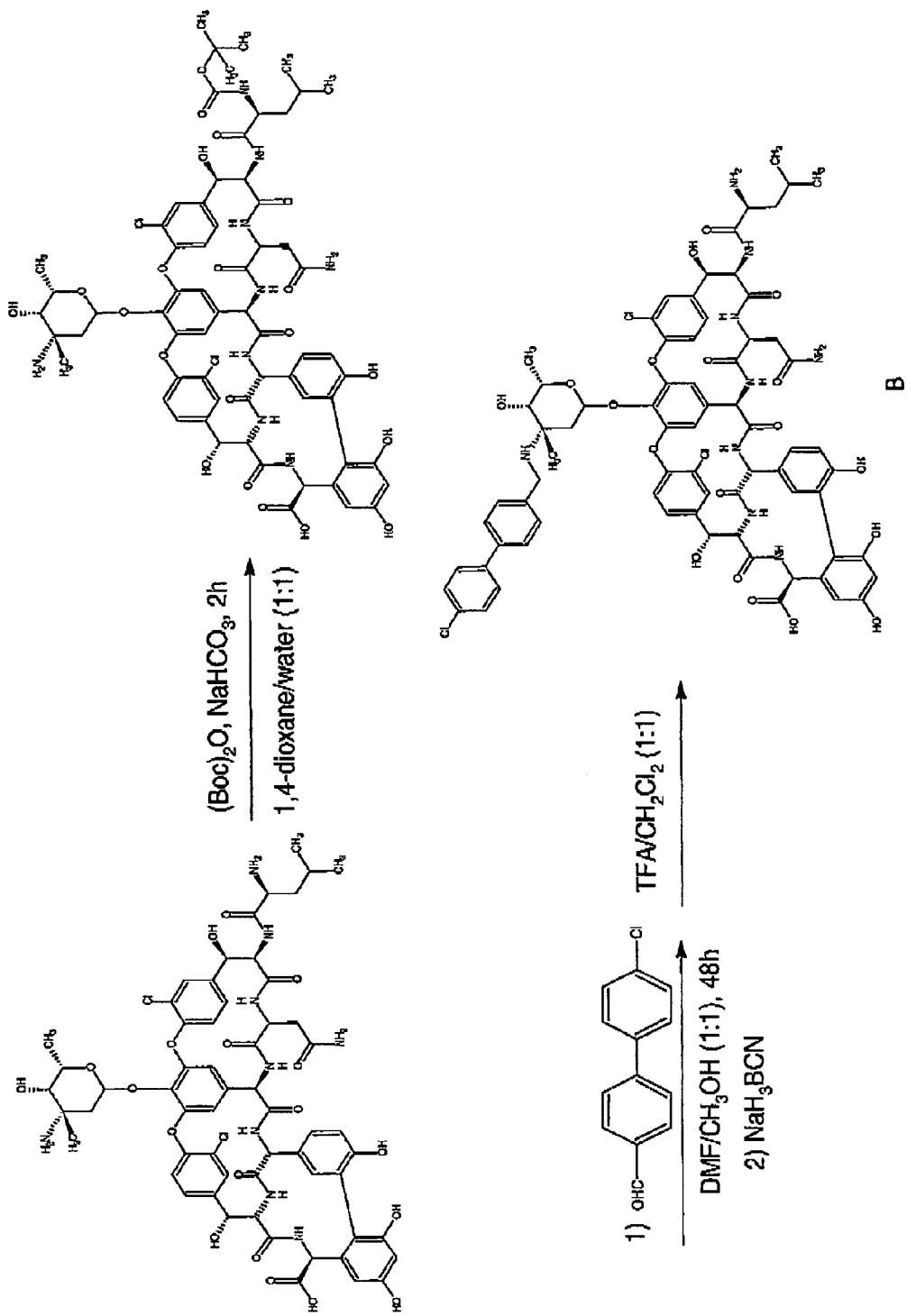
FIG. 2B is an example of a synthetic scheme for preparing a compound in accordance with the present invention.

DESCRIPTION OF SPECIFIC EMBODIMENTS
OF THE INVENTION

The materials and associated techniques and apparatuses of the present invention will now be described with reference to several embodiments. Important properties and characteristics of the described embodiments are illustrated in the structures in the text. While the invention will be described in conjunction with these embodiments, it should be understood that the invention it is not intended to be limited to these embodiments. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail in order not to unnecessarily obscure the present invention.

Introduction

The present invention provides novel semi-synthetic glycopeptides that have antibacterial activity. The semi-synthetic glycopeptides of the invention are based on modifications of a rearranged vancomycin or desmethyl-vancomycin scaffold, in particular, acylation or alkylation of the amino substituent on the amino-substituted sugar moiety on this scaffold with certain acyl or alkyl groups; and/or conversion of the acid moiety on the macrocyclic ring of this scaffolds to certain substituted amides. Also provided are methods for synthesis of the compounds, pharmaceutical compositions containing the compounds, and methods of use of the compounds for the treatment and/or prophylaxis of diseases, especially bacterial infections.

Compounds of the Invention

In specific embodiments of the invention, the rearranged vancomycin or desmethyl-vancomycin scaffold is modified to make compounds having the formula:

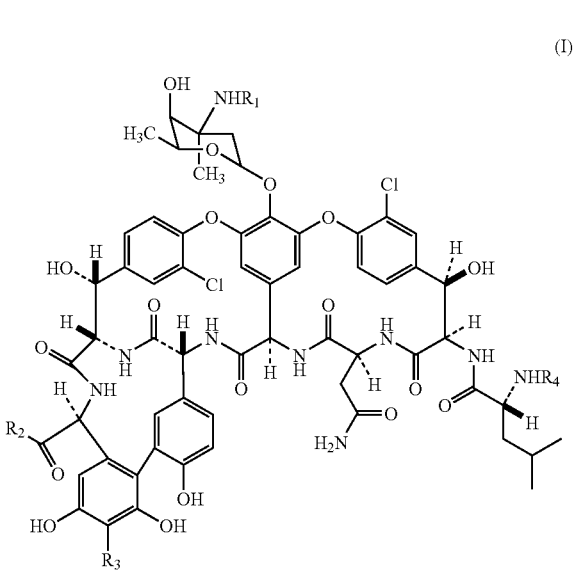

(I)

wherein, $R_1$ is selected from the group consisting of H, $CHR_5R_{5a}$, $C(=O)R_6$ and $C(=O)CR_7R_{7a}NR_8R_{8a}$, wherein, $R_5$ and $R_{5a}$ are independently selected from the group consisting of hydrogen and unsubstituted or substituted alkyl, alkenyl, cycloalkyl, cycloalkenyl, heterocycloalkyl, aryl, arylalkyl, alkylaryl, and heteroaryl, said aryl, alkylaryl, arylalkyl or heteroaryl group optionally containing one or more optionally substituted aryl, heteroaryl, or condensed rings, or $R_5$ and $R_{5a}$ together with the atom to which they are attached form a cycloalkyl ring which optionally contains a heteroatom selected from the group consisting of optionally substituted O, N, and S, $R_6$ is selected from the group consisting of unsubstituted or substituted alkyl, alkenyl, cycloalkyl, cycloalkenyl, heterocycloalkyl, aryl, arylalkyl, alkylaryl, and heteroaryl, said aryl, alkylaryl, arylalkyl or heteroaryl group optionally containing one or more optionally substituted aryl, heteroaryl, or condensed rings, $R_7$ and $R_{7a}$ are independently hydrogen, the side chain of a naturally occurring or non-naturally occurring amino acid, alkyl, or alkyl substituted with one or more substituents selected from the group consisting of halogen, hydroxy, alkoxy, alkoxyalkoxy, carboxyl, carboxyl ester, $-C(=O)NR_8R_{8a}$, $-NR_8R_{8a}$, aryl, substituted aryl, heteroaryl, substituted heteroaryl, mercapto, or thioalkoxy, or $R_7$ and $R_{7a}$ together with the atom to which they are attached form a cycloalkyl ring which optionally contains a heteroatom selected from the group consisting of optionally substituted O, N, and S;

$R_8$ and $R_{8a}$ are independently selected from the group consisting of hydrogen and unsubstituted or substituted alkyl, alkenyl, cycloalkyl, cycloalkenyl, heterocycloalkyl, aryl, arylalkyl, alkylaryl, and heteroaryl, said aryl, alkylaryl, arylalkyl or heteroaryl group optionally containing one or more optionally substituted aryl, heteroaryl, or condensed rings, or $R_8$ and $R_{8a}$ together with the atom to which they are attached form a cycloalkyl ring which optionally contains a heteroatom selected from the group consisting of optionally substituted O, N, and S;

$R_2$ is selected from the group consisting of,
(1) OH,
(2) 1-adamantanamino,
(3) 2-adamantanamino,
(4) 3-amino-1-adamantanamino,
(5) 1-amino-3-adamantanamino,
(6) 3-loweralkylamino-1-adamantanamino,
(7) 1-loweralkylamino-3-adamantanamino,
(8) amino,
(9) $NR_9R_{9a}$ wherein $R_9$ and $R_{9a}$ are independently selected from the group consisting of hydrogen, loweralkyl or substituted loweralkyl, or
  $R_9$ and $R_{9a}$ together with the atom to which they are attached form a 3-10 membered heterocycloalkyl ring, which may optionally be substituted with one or more substituents independently selected from the group consisting of
    (a) halogen,
    (b) hydroxy,
    (c) $C_1$-$C_3$-alkoxy,
    (d) $C_1$-$C_3$-alkoxy-$C_1$-$C_3$-alkoxy,
    (e) oxo,
    (f) $C_1$-$C_3$-alkyl,
    (g) halo-$C_1$-$C_3$-alkyl, and
    (h) $C_1$-$C_3$-alkoxy-$C_1$-$C_3$-alkyl;

$R_3$ is selected from the group consisting of hydrogen and aminoloweralkyl, wherein the aminoloweralkyl amino group is further substituted with unsubstituted or substituted alkyl, alkenyl, cycloalkyl, cycloalkenyl, aryl, arylalkyl, alkylaryl, alkoxy, aryloxy, substituted alkoxy, and substituted aryloxy; and $R_4$ is selected from the group consisting of hydrogen and methyl;

or a pharmaceutically acceptable salt, ester, solvate, stereoisomer, tautomer or prodrug thereof.

According to specific embodiments of the invention, the various substituents may be as follows:

Within $R_1$:

$R_5$ may be hydrogen and $R_{5a}$ may be selected from the group consisting of unsubstituted or substituted alkyl, alkenyl, cycloalkyl, cycloalkenyl, heterocycloalkyl, aryl, arylalkyl, alkylaryl, and heteroaryl, said aryl, alkylaryl, arylalkyl or heteroaryl group optionally containing one or more optionally substituted aryl, heteroaryl, or condensed rings, or $R_5$ and $R_{5a}$ together with the atom to which they are attached form a cycloalkyl ring which optionally contains a heteroatom selected from the group consisting of optionally substituted O, N, and S. In specific embodiments, $R_{5a}$ may be an unsubstituted or substituted biphenyl, for example chloro-biphenyl.

$R_6$ may be β-amino acid analog. Such a group will include a $-CH_2CHNH-$ portion. For example, $R_6$ may be $CH_2C(R_7)(R_{7a})(NR_8R_{8a})$ wherein $R_7$, $R_{7a}$, $R_8$, and $R_{8a}$ are previously defined or $-CR_7R_{7a}$ together with $NR_8R_{8a}$ form a pyrrolidine ring.

The $C(=O)CR_7R_{7a}NR_8R_{8a}$ substituent may be an amino acid moiety, such that $R_7$, $R_8$ and $R_{8a}$ are each H, $CH_3$, $CH(CH_3)_2$, $CH_2CH(CH_3)_2$, $CH(CH_3)CH_2CH_3$, $(CH_2)_4NH_2$, $CH_2OH$, $CH(OH)CH_3$, $CH_2COOH$, $(CH_2)_2COOH$, $CH_2C(=O)NH_2$, $(CH_2)_2C(=O)NH_2$, $CH_2SH$, $(CH_2)_2SCH_3$, $(CH_2)_3NHC(=NH)NH_2$, $CH_2C_6H_5$, $CH_2C_6H_4OH$, $CH_2$(4-imidazoyl) and $CH_2$(3-indolyl), or $-CR_7R_{7a}$ together with $NR_8R_{8a}$ form a pyrrolidine ring.

Alternatively, $R_7$ may be H and $R_{7a}$ may be selected from the group consisting of
(1) hydrogen,
(2) $C_1$-$C_{12}$-alkyl, and
(3) $C_1$-$C_{12}$-alkyl substituted with one or more substituents selected from the group consisting of
  (a) halogen,
  (b) hydroxy,
  (c) $C_1$-$C_3$-alkoxy,
  (d) $C_1$-$C_3$-alkoxy-$C_1$-$C_3$-alkoxy,
  (e) $-CO_2R_5$ wherein $R_5$ is hydrogen, loweralkyl or substituted loweralkyl,
  (f) $-C(=O)NR_9R_{9a}$)
  (g) amino, and
  (h) $-NR_9R_{9a}$, or
    $R_9$ and $R_{9a}$ together with the atom to which they are attached form a 3-10 membered heterocycloalkyl ring optionally substituted with one or more substituents independently selected from the group consisting of
      (i) halogen.
      (ii) hydroxy,
      (iii) $C_1$-$C_3$-alkoxy,
      (iv) $C_1$-$C_3$-alkoxy-$C_1$-$C_3$-alkoxy,
      (v) oxo,
      (vi) $C_1$-$C_3$-alkyl,
      (vii) halo-$C_1$-$C_3$-alkyl, and
      (viii) $C_1$-$C_3$-alkoxy-$C_1$-$C_3$-alkyl,
  (i) aryl,
  (j) substituted aryl,
  (k) heteroaryl, (l) substituted heteroaryl,
(m) mercapto, and
(n) $C_1$-$C_3$-thioalkoxy.

In addition, $R_8$ and $R_{8a}$ may be independently selected from the group consisting of,
(1) hydrogen,
(2) $C_1$-$C_{12}$-alkyl,
(3) $C_2$-$C_{12}$-alkyl substituted with one or more substituents selected from the group consisting of
  (a) halogen,
  (b) hydroxy,
  (c) $C_1$-$C_3$-alkoxy,
  (d) $C_1$-$C_3$-alkoxy-$C_1$-$C_3$-alkoxy,
  (e) amino, and
  (f) $C_1$-$C_3$-alkylamino,
(4) $C_1$-$C_{12}$-alkyl substituted with aryl,
(5) $C_1$-$C_{12}$-alkyl substituted with substituted aryl,
(6) $C_1$-$C_{12}$-alkyl substituted with heteroaryl, and
(7) $C_1$-$C_{12}$-alkyl substituted with substituted heteroaryl; or
$R_8$ and $R_{8a}$ together with the atom to which they are attached form a $C_3$-$C_7$-cycloalkyl ring which, when the ring is a 5- to 7-membered ring, optionally contains a hetero function selected from the group consisting of —O—, —NH, —N($C_1$-$C_6$-alkyl-)-, —N(aryl)-, —N(aryl-$C_1$-$C_6$-alkyl-)-, —N(substituted-aryl-$C_1$-$C_6$-alkyl-)-, —N(heteroaryl)-, —N(heteroaryl-$C_1$-$C_6$-alkyl-)-, —N(substituted-heteroaryl-$C_1$-$C_6$-alkyl-)-, and —S— or $S(=O)_n$— wherein n is 1 or 2.

Definitions

Unless otherwise noted, terminology used herein should be given its normal meaning as understood by one of skill in the art. In order to facilitate understanding of the present invention, a number of defined terms are used herein to designate particular elements of the present invention. When so used, the following meanings are intended:

The term "alkyl" as used herein refers to saturated, straight- or branched-chain hydrocarbon radicals derived from a hydrocarbon moiety containing between one and twenty carbon atoms by removal of a single hydrogen atom.

The term "alkenyl" as used herein refers to unsaturated, straight- or branched-chain hydrocarbon radicals derived from a hydrocarbon moiety containing between two and twenty carbon atoms by removal of a single hydrogen atom.

The term "cycloalkyl" as used herein refers to a monovalent group derived from a monocyclic or bicyclic saturated carbocyclic ring compound containing between three and twenty carbon atoms by removal of a single hydrogen atom.

The term "cycloalkenyl" as used herein refers to a monovalent group derived from a monocyclic or bicyclic unsaturated carbocyclic ring compound containing between three and twenty carbon atoms by removal of a single hydrogen atom.

The terms "$C_1$-$C_3$-alkyl", "$C_1$-$C_6$-alkyl", and "$C_1$-$C_{12}$-alkyl" as used herein refer to saturated, straight- or branched-chain hydrocarbon radicals derived from a hydrocarbon moiety containing between one and three, one and six, and one and twelve carbon atoms, respectively, by removal of a single hydrogen atom. Examples of $C_1$-$C_3$-alkyl radicals include methyl, ethyl, propyl and isopropyl. Examples of $C_1$-$C_6$-alkyl radicals include, but not limited to, methyl, ethyl, propyl, isopropyl, n-butyl, tert-butyl, neopentyl and n-hexyl. Examples of $C_1$-$C_{12}$-alkyl radicals include, but not limited to, methyl, ethyl, propyl, isopropyl, n-butyl, tert-butyl, neopentyl, n-hexyl, n-heptyl, n-octyl, n-nonyl, n-decyl, n-undecyl and n-docecyl.

The term substituted loweralkyl as used herein refers to $C_1$-$C_{12}$-alkyl substituted by one, two or three groups consisting of halogen, alkoxy, amino, alkylamino, dialkylamino, hydroxy, aryl, heteroaryl, alkene or alkyne groups.

The term "$C_3$-$C_{12}$-cycloalkyl" denotes a monovalent group derived from a monocyclic or bicyclic saturated carbocyclic ring compound by removal of a single hydrogen atom. Examples include cyclopropyl, cyclobutyl, cyclopentyl, cyclohexyl, bicyclo[2.2.1]heptyl, and bicyclo[2.2.2]octyl.

The terms "$C_1$-$C_3$-alkoxy", "$C_1$-$C_6$-alkoxy" as used herein refers to the $C_1$-$C_3$-alkyl group and $C_1$-$C_6$-alkyl group, as previously defined, attached to the parent molecular moiety through an oxygen atom. Examples of $C_1$-$C_6$-alkoxy radicals include, but not limited to, methoxy, ethoxy, propoxy, isopropoxy, n-butoxy, tert-butoxy, neopentoxy and n-hexoxy.

The term "oxo" denotes a group wherein two hydrogen atoms on a single carbon atom in an alkyl group as defined above are replaced with a single oxygen atom (i.e., a carbonyl group).

The term "aryl" as used herein refers to a mono- or bicyclic carbocylic ring system having one or two aromatic rings including, but not limited to, phenyl, naphthyl, tetrahydronaphthyl, indanyl, indenyl and the like and can be un-substituted or substituted (including bicyclic aryl groups) with one, two or three substituents independently selected from loweralkyl, substituted loweralkyl, haloalkyl, $C_1$-$C_{12}$-alkoxy, thioalkoxy, $C_1$-$C_{12}$-thioalkoxy, aryloxy, amino, alkylamino, dialkylamino, acylamino, cyano, hydroxy, halogen, mercapto, nitro, carboxaldehyde, carboxy, alkoxycarbonyl and carboxamide. In addition, substituted aryl groups include tetrafluorophenyl and pentafluorophenyl.

The term "arylalkyl" as used herein refers to an aryl group as defined above attached to the parent molecular moiety through an alkyl group wherein the alkyl group is of one to twelve carbon atoms.

The term "alkylaryl" as used herein refers to an alky group as defined above attached to the parent molecular moiety through an aryl group.

The term "halo" and "halogen" as used herein refer to an atom selected from fluorine, chlorine, bromine and iodine.

The term "alkylamino" refers to a group having the structure —NHR' wherein R' is alkyl, as previously defined. Examples of alkylamino include methylamino, ethylamino, iso-propylamino, and the like.

The term "loweralkylamino" as used herein refers to $C_1$-$C_6$-alkyl groups, as previously defined, attached to the parent molecular moiety through a nitrogen atom. Examples of $C_1$-$C_3$-alkylamino include, but are not limited to methylamino, dimethylamino, ethylamino, diethylamino, and propylamino.

The term "dialkylamino" refers to a group having the structure —NHR'R" wherein R' and R" are independently selected from alkyl, as previously defined. Additionally, R' and R" taken together may optionally be —$(CH_2)_k$— where k is an integer of from 2 to 6. Examples of dialkylamino include dimethylamino, diethylamino, methylpropylamino, piperidino, and the like.

The term "haloalkyl" denotes an alkyl group, as defined above, having one, two or three halogen atoms attached thereto and is exemplified by such group as chloromethyl, bromoethyl, trifluoromethyl, and the like.

The term "alkoxycarbonyl" represents as ester group; i.e. an alkoxy group, attached to the parent molecular moiety through a carbonyl group such as methoxycarbonyl, ethoxycarbonyl, and the like.

The term "thioalkoxy" refers to an alkyl group previously defined attached to the parent molecular moiety through a sulfur atom.

The term "carboxaldehyde" as used herein refers to a group of formula —CHO.

The term "carboxy" as used herein refers to a group of formula —$CO_2H$.

The term "carboxamide" as used herein refers to a group of formula —CONHR'R" wherein R' and R" are independently selected from hydrogen, alkyl, or R' and R" taken together may optionally be —$(CH_2)_k$— where k is an integer of from 2 to 6.

The term "heteroaryl", as used herein, refers to a cyclic or bicyclic aromatic radical having from five to ten ring atoms in each ring of which at least one atom of the cyclic or bicyclic ring is selected from optionally substituted S, O, and N; zero, one or two ring atoms are additional heteroatoms independently selected from optionally substituted S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, naphthyridinyl; and the like.

The term "heterocycloalkyl" as used herein, refers to a non-aromatic partially unsaturated or fully saturated 3- to 10-membered ring system, which includes single rings of 3 to 8 atoms in size and bi- or tri-cyclic ring systems which may include aromatic six-membered aryl or heteroaryl rings fused to a non-aromatic ring. These heterocycloalkyl rings include those having from one to three heteroatoms independently selected from oxygen, sulfur and nitrogen, in which the nitrogen and sulfur heteroatoms may optionally be oxidized and the nitrogen heteroatom may optionally be quaternized. Representative heterocycloalkyl rings include, but not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "heteroarylalkyl" as used herein, refers to a heteroaryl group as defined above attached to the parent molecular moiety through an alkyl group wherein the alkyl group is of one to twelve carbon atoms.

"Protecting group" refers to an easily removable group which is known in the art to protect a functional group, for example, a hydroxyl, ketone or amine, against undesirable reaction during synthetic procedures and to be selectively removable. The use of protecting groups is well known in the art for protecting groups against undesirable reaction during synthetic procedure and many such protecting groups are known, cf., for example, T. H. Greene and P. G. M. Wuts, *Protective Groups in Organic Synthesis*, 2nd edition, John Wiley & Sons, New York (1991). Examples of hydroxy-protecting groups include, but are not limited to, methylthiomethyl, tert-dimethylsilyl, tert-butyldiphenylsilyl, ethers such as methoxymethyl, and esters including acetyl, benzoyl, and the like. Examples of ketone protecting groups include, but are not limited to, ketals, oximes, O-substituted oximes for example O-benzyl oxime, O-phenylthiomethyl oxime, 1-isopropoxycyclohexyl oxime, and the like. Examples of amine protecting groups include, but are not limited to, tert-butoxycarbonyl (Boc) and carbobenzyloxy (Cbz).

The term amino acid refers to amino acids having D or L stereochemistry, and also refers to synthetic, non-natural amino acids having side chains other than those found in the 20 common amino acids. Non-natural amino acids are commercially available or may be prepared according to U.S. Pat. No. 5,488,131 and references therein. Amino acids may be further substituted to contain modifications to their amino, carboxy, or side chain groups. These modifications include the numerous protecting groups commonly used in peptide synthesis (T. H. Greene and P. G. M. Wuts, *Protective Groups in Organic Synthesis*, 2nd edition, John Wiley & Sons, New York, 1991).

The term "substituted aryl" as used herein, refers to an aryl group as defined herein substituted by independent replacement of one, two or three of the hydrogen atoms thereon with Cl, Br, F, I, OH, CN, $C_1$-$C_{12}$-alkyl, $C_1$-$C_{12}$-alkoxy, $C_1$-$C_{12}$-alkoxy substituted with aryl, C1-C12-alkoxy substituted with substituted aryl, haloalkyl, thioalkyl, amino, alkylamino, dialkylamino, mercapto, nitro, carboxaldehyde, carboxy, alkoxycarbonyl and carboxamide. In addition, any one substituent may be an aryl, heteroaryl, or hetercycloalkyl group.

The term "substituted heteroaryl" as used herein, refers to a heteroaryl group as defined herein substituted by independent replacement of one, two or three of the hydrogen atoms thereon with Cl, Br, F, I, OH, CN, $C_1$-$C_{12}$-alkyl, $C_1$-$C_{12}$-alkoxy, $C_1$-$C_{12}$-alkoxy substituted with aryl, haloalkyl, thioalkyl, amino, alkylamino, dialkylamino, mercapto, nitro, carboxaldehyde, carboxy, alkoxycarbonyl and carboxamide. In addition, any one substituent may be an aryl, heteroaryl, or hetercycloalkyl group.

The term "substituted heterocycloalkyl" as used herein, refers to a heterocycloalkyl group as defined herein substituted by independent replacement of one, two or three of the hydrogen atoms thereon with Cl, Br, F, I, OH, CN, $C_1$-$C_{12}$-alkyl, $C_1$-$C_{12}$-alkoxy, $C_1$-$C_{12}$-alkoxy substituted with aryl, haloalkyl, thioalkyl, amino, alkylamino, dialkylamino, mercapto, nitro, carboxaldehyde, carboxy, alkoxycarbonyl and carboxamide. In addition, any one substituent may be an aryl, heteroaryl, or hetercycloalkyl group.

The term "adamantanamino" as used herein, refers to a fully saturated tricyclo [3.3.1.1(3,7)] 10-membered carbon ring system with one or more amino substituents. Examples include 1-adamantanamino, 2-adamantanamino, 3-amino-1-adamantanamino, 1-amino-3-adamantanamino, 3-loweralkylamino-1-adamantanamino, and 1-loweralkylamino-3-adamantanamino.

The term "stereoisomer" as used herein, refers to either of two forms of a compound having the same molecular formula and having their constituent atoms attached in the same order, but having different arrangement of their atoms in space about an asymmetric center. Numerous asymmetric centers may exist in the compounds of the present invention. Except where otherwise noted, the present invention contemplates the various stereoisomers and mixtures thereof. Accordingly, except where otherwise noted, it is intended that a mixture of stereo-orientations or an individual isomer of assigned or unassigned orientation may be present.

The term "tautomer" as used herein refers to either of the two forms of a chemical compound that exhibits tautomerism, which is the ability of certain chemical compounds to exist as a mixture of two interconvertible isomers in equilibrium via hydrogen transfer. The keto and enol forms of carbonyl compounds are examples of tautomers. They are interconvertible in the presence of traces of acids and bases via a resonance stabilized anion, the enolate ion.

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in J. Pharmaceutical Sciences, 66: 1-19 (1977), incorporated herein by reference. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

The term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Representative examples of particular esters include, but are not limited to, formates, acetates, propionates, butyrates, acrylates and ethylsuccinates.

The term "solvate" as used herein refers to a compound formed by solvation, the combination of solvent molecules with molecules or ions of solute composed of a compound according to the present invention. The term "pharmaceutically acceptable solvate" refers to those solvates which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable solvates are well known in the art.

The term "pharmaceutically acceptable prodrugs" refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

Synthetic Methods

Synthesis of the compounds of the invention can be broadly summarized as follows. The compounds of the invention may be made by coupling functionalized or unfunctionalized glycopeptides with the appropriate alkyl, acyl and/or amino groups under amide formation conditions. In particular, the semi-synthetic glycopeptides of the invention may be made by modifying a scaffold having the formula (IA), referred to herein as "rearranged" vancomycin or desmethyl-vancomycin:

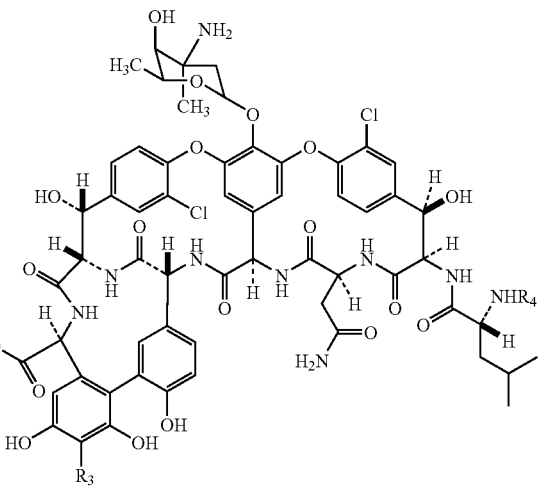

(IA)

The rearranged vancomycin or desmethyl-vancomycin starting material is synthesized by removing the inner sugar moiety of vancomycin or desmethyl-vancomycin. To accomplish this, vancomycin or desmethyl-vancomycin may be heated, for example to between about 40 and 120° C., in the presence of acid, for example trifluoroacetic acid (TFA). A specific example is described in Example 1, below. The vancomycin or desmethyl-vancomycin starting material may be unsubstituted or substituted at $R_3$ with an aminoloweralkyl group.

Modification of the rearranged scaffold is by acylation or alkylation of the amino substituent on the amino-substituted sugar moiety on this scaffold with certain acyl or akyl groups groups; and/or conversion of the acid moiety on the macrocyclic ring of this scaffolds to certain substituted amides. In specific embodiments, the compounds of the invention may generally be made by coupling a suitably functionalized or unfunctionalized rearranged vancomycin or desmethyl-vancomycin glycopeptide with the appropriate starting materials using alkylation, amino acid coupling, or acylation procedures known to one of skill in the art. Synthesis of compounds may also involve the use of protecting groups in order to maximize yields, minimize unwanted side products, or improve the ease purification.

$R_1$ alkyl groups may be formed by contacting the glycopeptide with an aldehyde or ketone followed by reductive amination of the resulting imine. $R_1$ groups linked to the glycopeptide with an amide bond may be formed by reacting the glycopeptide with the appropriate starting material containing a carboxylic acid or activated carboxylic acid moiety under known amide forming conditions.

Substitutions at $R_2$ may be introduced by reacting an amine with the glycopeptide under known amide forming conditions.

Substitutions at $R_3$ may be introduced via a Mannich reaction wherein the glycopeptide is treated with an amine and formaldehyde under basic conditions (for example, as described in The Journal of Antibiotics, Vol. 50, No. 6, p. 509-513).

Specific examples of syntheses for compounds in accordance with the present invention are provided in Example 2, below. Other compounds in accordance with the present invention can be prepared in an analogous manner.

In general, compounds in accordance with the present invention may be made by modifying a compound having the formula,

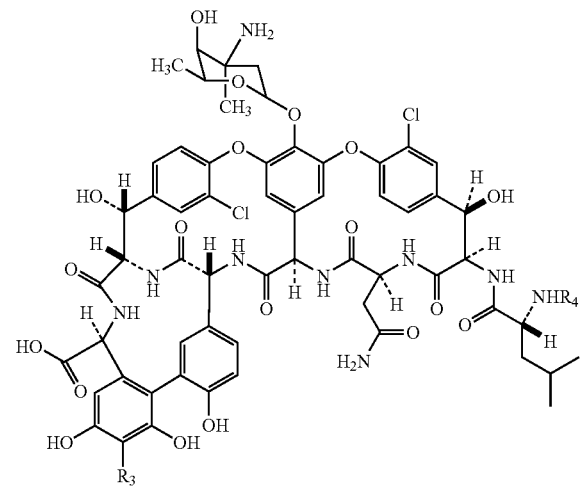

(IA)

by one of the following techniques:

(a) acylation of the amino substituent on the amino-substituted sugar moiety of the compound with an acyl group having the structure,

—C(=O)CR$_7$R$_{7a}$NR$_8$R$_{8a}$, (b) acylation of the amino substituent on the amino-substituted sugar moiety of the compound with an acyl group having the structure,

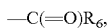
—C(=O)R$_6$, (c) alkylation of the amino substituent on the amino-substituted sugar moiety of the compound with an alkyl group having the structure,

CHR$_5$R$_{5a}$, (d) conversion of the acid moiety on the macrocyclic ring of the compound with a substituted amide as defined by $R_2$, and (e) a combination of (a) and (d)
(f) a combination of (b) and (d)
(g) a combination of (c) and (d)

to form a compound having the formula,

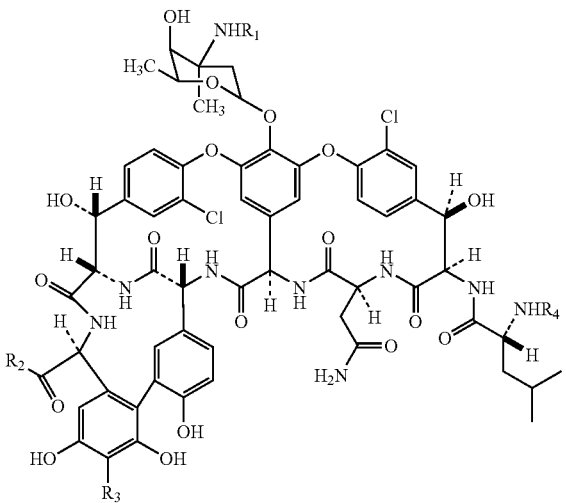

(I)

wherein $R_1$, $R_2$, $R_3$, $R_4$, $R_5$, $R_{5a}$, $R_6$, $R_7$, $R_{7a}$, $R_8$, and $R_{8a}$ have the meanings defined herein.

Pharmaceutical Compositions and Treatment

Pharmaceutical compositions of the present invention comprise a therapeutically effective amount of a compound of the present invention formulated together with one or more pharmaceutically acceptable carriers. Such pharmaceutical compositions may be used to treat bacterial infections in a host mammal in need of such treatment by administering to a mammal in need of such treatment a therapeutically effective amount of a compound of the invention.

As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), bucally, or as an oral or nasal spray, or a liquid aerosol or dry powder formulation for inhalation.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form may be accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations may also be prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, acetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulations, ear drops, and the like are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Compositions of the invention may also be formulated for delivery as a liquid aerosol or inhalable dry powder. Liquid aerosol formulations may be nebulized predominantly into particle sizes that can be delivered to the terminal and respiratory bronchioles where bacteria reside in patients with bronchial infections, such as chronic bronchitis and pneumonia. Pathogenic bacteria are commonly present throughout airways down to bronchi, bronchioli and lung parenchema, particularly in terminal and respiratory bronchioles. During exacerbation of infection, bacteria can also be present in alveoli. Liquid aerosol and inhalable dry powder formulations are preferably delivered throughout the endobronchial tree to the terminal bronchioles and eventually to the parenchymal tissue.

Aerosolized formulations of the invention may be delivered using an aerosol forming device, such as a jet, vibrating porous plate or ultrasonic nebulizer, preferably selected to allow the formation of a aerosol particles having with a mass medium average diameter predominantly between 1 to 5μ. Further, the formulation preferably has balanced osmolarity ionic strength and chloride concentration, and the smallest aerosolizable volume able to deliver effective dose of the compounds of the invention to the site of the infection. Additionally, the aerosolized formulation preferably does not impair negatively the functionality of the airways and does not cause undesirable side effects.

Aerosolization devices suitable far administration of aerosol formulations of the invention include, for example, jet, vibrating porous plate, ultrasonic nebulizers and energized dry powder inhalers, that are able to nebulize the formulation of the invention into aerosol particle size predominantly in the size range from 1-5μ. Predominantly in this application means that at least 70% but preferably more than 90% of all generated aerosol particles are within 1-5μ range. A jet nebulizer works by air pressure to break a liquid solution into aerosol droplets. Vibrating porous plate nebulizers work by using a sonic vacuum produced by a rapidly vibrating porous plate to extrude a solvent droplet through a porous plate. An ultrasonic nebulizer works by a piezoelectric crystal tat shears a liquid into small aerosol droplets. A variety of suitable devices are available, including, for example, vibrating porous plate nebulizers sold under the trademarks AERONEB™ and AERODOSE™ (AeroGen, Inc., Sunnyvale, Calif.), jet nebulizers sold under the trademark SIDESTREAM® (Medic-Aid Ltd., West Sussex, England), and under the trademarks PARI LC® and PARI LC STAR® (Pari Respiratory Equipment, Inc., Richmond, Va.), and ultrasonic nebulizers sold under the trademarks AEROSONIC™ (DeVilbiss Medizinische Produkte (Deutschland) GmbH, Heiden, Germany) and ULTRAAIRE® (Omron Healthcare, Inc., Vernon Hills, Ill).

Compounds of the invention may also be formulated for use as topical powders and sprays that can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, bacterial infections are treated or prevented in a patient such as a human or lower mammal by administering to the patient a therapeutically effective amount of a compound of the invention, in such amounts and for such time as is necessary to achieve the desired result. By a "therapeutically effective amount" of a compound of the invention is meant a sufficient amount of the compound to treat bacterial infections, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of this invention administered to a human or other mammal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 2000 mg of the compound(s) of this invention per day in single or multiple doses.

EXAMPLES

The following examples provide details concerning the synthesis, properties and activities and applications of semi-synthetic glycopeptides in accordance with the present invention. It should be understood the following is representative only, and that the invention is not limited by the detail set forth in these examples.

Example 1

Synthesis of Starting Material

A starting material for preparing a compound in accordance with the present invention, a modified desmethyl-vancomycin derivative, was synthesized as illustrated in and described with respect to FIG. 1.

Synthesis of Compound A. Desmethyl-vancomycin hydrochloride (5 g) was dissolved in TFA (20 mL). The solution was stirred at 50° C. for 2 hours, and concentrated under vacuum. The final oily solid was dissolved in 20 mL of acetone and then poured into 200 mL of chloroform. The precipitate was washed two times with 20 mL chloroform and dried under vacuum. The precipitated solid was purified by reverse-phase column chromatography, yielding of the compound A (500 mg, 10%).

Example 2

Synthesis of Inventive Compound (B)

Compound B, a compound in accordance with the present invention, was synthesized by alternative methods (methods A and B) as illustrated in and described with respect to FIGS. 2A, and 2B, respectively.

Method A:

Synthesis of Cbz-A. To a solution of compound A (0.10 mmol) and $NaHCO_3$ (0.20 mmol) in 1,4-dioxane/water (1:1, 5 mL) was added benzyloxycarbonyl chloride (Cbz-Cl) (0.11 mmol) in small portions dropwise under ice cooling. The reaction mixture was stirred at room temperature for 1 hour, and then poured into 75 mL of acetone. The precipitate was washed two times with 10 mL of acetone, dried under vacuum.

Synthesis of Cbz-A-4-Chlorophenylbenzyl. Cbz-A (0.10 mmol), 4-chloro-biphenylcarboxaldehyde (0.15 mmol) was dissolved in DMF/MeOH (1:1, 5 mL). The reaction solution was stirred at 65° C. for 48 hours. Sodium cyanoborohydride (0.20 mmol) was added and stirred for additional 24 hours. The reaction solution was cooled down and poured into 75 mL of acetone. The precipitate was collected and dried.

Synthesis of compound B. The solid of Cbz-A-4-chlorophenylbenzyl (0.10 mmol) was dissolved in 7 mL of DMF. Pd/C (5%, 50 mg) was added. The mixture was hydrogenated (~1 atm, room temperature) for 3 hours. The catalyst was filtered off and the solution was pooled into 80 mL of acetone. The precipitated solid was collected and purified by reverse-phase column chromatography.

Method B:

Synthesis of Boc-A. To a solution of compound A (0.10 mmol), benzyloxycarbonyl chloride (Cbz-Cl, 0.11 mmol) in 5 mL of 1,4-dioxane/water (1:1), NaHCO$_3$ (0.20 mmol) was added. The reaction mixture was stirred at room temperature for 6 hours, and then poured into 75 mL of acetone. The precipitate was washed two times with 10 mL of acetone, dried under vacuum.

Synthesis of Boc-A-4-chloro-phenylbenzyl. NCPC004850-Boc (0.10 mmol) and 4-chloro-biphenylcarboxaldehyde (0.15 mmol) was dissolved in DMF/MeOH (1:1, 5 mL). The reaction solution was stirred at 65° C. for 48 hours. Sodium cyanoborohydride (0.20 mmol) was added and stirred for another 24 hours. The reaction solution was cooled down and poured into 75 mL of acetone. The precipitate was collected and dried.

Synthesis of compound B. The above precipitate (0.10 mmol) was suspended in 10 mL of chloroform. TFA (2 mL) was dropped slowly into the solution. The solution was stirred at room temperature for 20 min and poured into ether (50 mL). The precipitate was washed with 10 mL of ether. The precipitated solid was collected and purified by reverse-phase column chromatography.

Table

The following table identifies specific species of compounds according to the present invention and information concerning their associated antibacterial activity. The antibacterial activity of a compound in accordance with the present invention, chloro-biphenyl-rearranged norvacomycin (B), was tested and compared to unmodified vancomycin (Van) and norvancoycin (Nor). MIC (minimum inhibitory concentration) was measured according to NCCLS standards using the microdilution broth prodcedure. Serial dilutions of the compounds were placed in a 96-well microplate containing Mueller-Hinton medium. Based on absorbance of 600 nm, diluted overnight cultures were placed in the wells at a final concentration of 5×10$^5$ cfu/mL. The plate was then placed in a culture box at 35° C. The next day, MIC was determined by visual observation of the plates. The glycopeptides were tested against a variety of strains well known in the art for such testing, including methicillin-susceptible Staphylococus aureus (MSSA), methicillin-susceptible Staphylococus epidermidis (MSSE), methicllin-resistant Staphylococus aureus (MRSA), methicllin-resistant Staphylococus epidermidis (MRSE), and glycopeptide-intermediate Staphylococus aureus (GISA). Results are shown in the Table 1 as minimum inhibitory concentration (MIC) in units of µg/ml:

TABLE 1

| STRAIN TYPE | STRAIN # | Antibacterial Activity GLYCOPETIDE | | |
|---|---|---|---|---|
| | | Van | Nor | A |
| MSSA | 68 | 2 | 2 | 1 |
| | 83 | 2 | 2 | <0.25 |
| MRSA | 134 | 2 | 2 | <0.25 |
| | 143 | 2 | 2 | 0.5 |
| MSSE | 3 | 2 | 2 | 0.5 |
| | 10 | 2 | 2 | 0.5 |
| MRSE | 24 | 2 | 2 | 1 |
| | 25 | 2 | 2 | 0.5 |
| | 26 | 2 | 2 | 0.5 |
| GISA (V) | 68 | 8 | 4 | 1 |
| | 143 | 8 | 8 | 1 |
| GISA (D) | 68 | 8 | 4 | 2 |
| | 143 | 4 | 4 | 1 |

CONCLUSION

Although the foregoing invention has been described in some detail for purposes of clarity of understanding, it will be apparent that certain changes and modifications may be practiced within the scope of the appended claims. It should be noted that there are many alternative ways of implementing both the processes and compositions of the present invention. Accordingly, the present embodiments are to be considered as illustrative and not restrictive, and the invention is not to be limited to the details given herein, but may be modified within the scope and equivalents of the appended claims.

What is claimed is:

1. A compound, wherein the compound is:

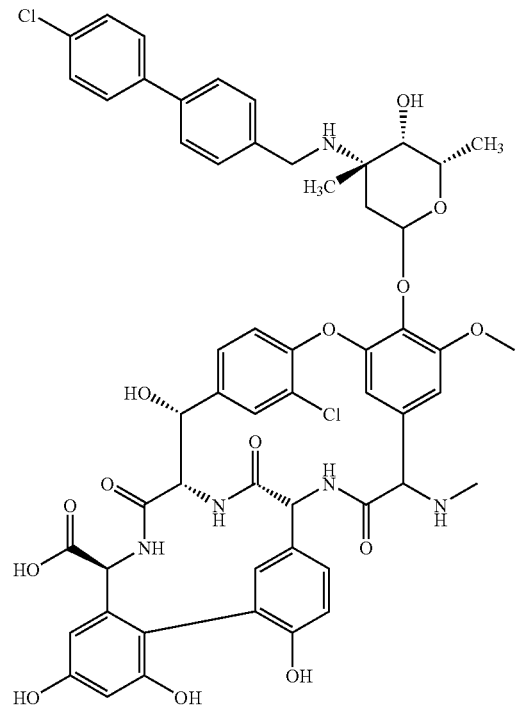

-continued
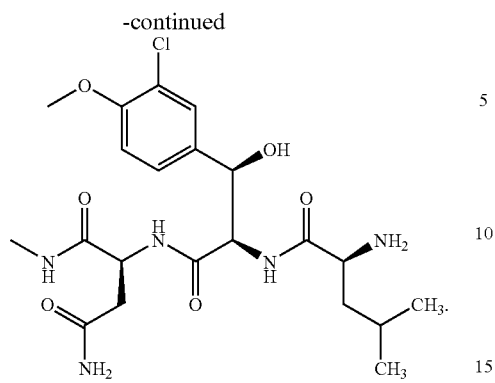
2. A pharmaceutical composition comprising a therapeutically effective amount of a compound, together with a pharmaceutically acceptable carrier, wherein the compound is:
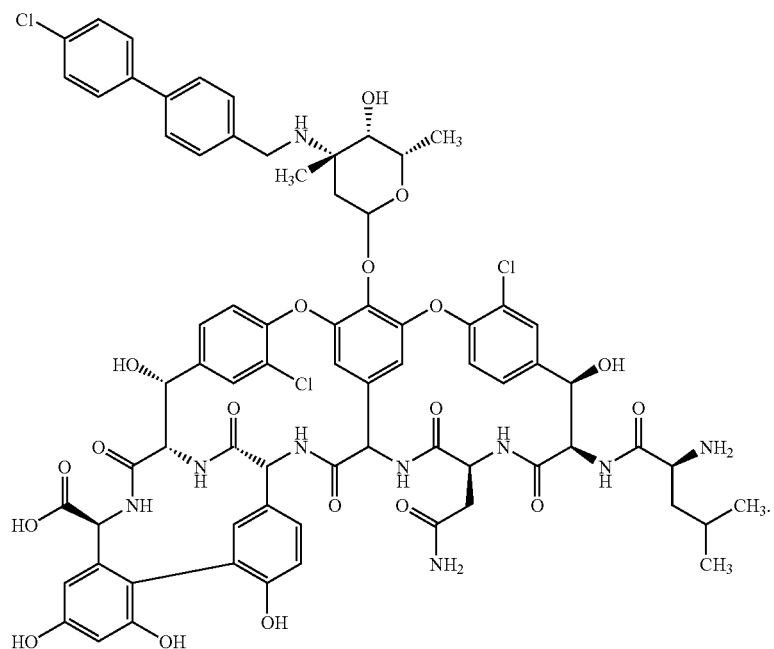
* * * * *

UNITED STATES PATENT AND TRADEMARK OFFICE
CERTIFICATE OF CORRECTION

PATENT NO.        : 7,368,422 B2                                    Page 1 of 1
APPLICATION NO.   : 11/361311
DATED             : May 6, 2008
INVENTOR(S)       : Lei et al.

It is certified that error appears in the above-identified patent and that said Letters Patent is hereby corrected as shown below:

CLAIMS:

In claim 1 (column 20, line 40-66, column 21, line 1-16) the formula should appear as follows:

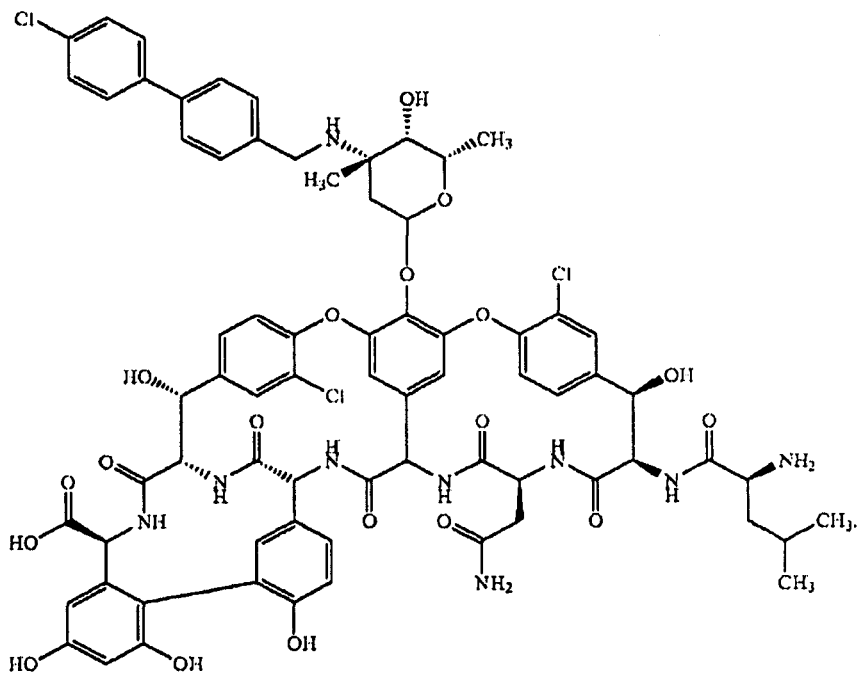

Signed and Sealed this

Seventeenth Day of August, 2010

David J. Kappos
*Director of the United States Patent and Trademark Office*